United States Patent [19]
Keary et al.

[11] Patent Number: 4,657,676
[45] Date of Patent: Apr. 14, 1987

[54] SEDIMENTATION FIELD FLOW FRACTIONATION

[75] Inventors: Colin M. Keary, Aberdeen, Scotland; David Shepherd, Thelwall, England

[73] Assignee: Imperial Chemical Industries PLC, London, England

[21] Appl. No.: 447,941

[22] Filed: Dec. 8, 1982

[30] Foreign Application Priority Data

Dec. 8, 1981 [GB] United Kingdom ............... 8136982

[51] Int. Cl.$^4$ ..................... B03B 5/62; B01D 15/08
[52] U.S. Cl. ................................. 210/198.2; 73/30; 209/1; 209/155; 210/511
[58] Field of Search ............ 210/657, 781, 782, 198.2, 210/511; 55/17, 67, 386; 209/1, 155; 73/30

[56] References Cited

U.S. PATENT DOCUMENTS

| | | | |
|---|---|---|---|
| 2,422,882 | 6/1947 | Bramlet | 55/17 |
| 3,050,984 | 8/1962 | Nerheim et al. | 73/30 |
| 3,503,712 | 3/1970 | Sussman | 210/198.2 |
| 3,535,918 | 10/1970 | Munk | 210/198.2 |
| 4,139,458 | 2/1979 | Harrison | 210/198.2 |
| 4,258,550 | 7/1981 | Watts | 55/17 |
| 4,283,276 | 8/1981 | Grant | 209/155 |
| 4,287,061 | 9/1981 | Sutherland | 210/198.2 |

FOREIGN PATENT DOCUMENTS

| | | |
|---|---|---|
| 0035394 | 9/1981 | European Pat. Off. |
| 0035395 | 9/1981 | European Pat. Off. |
| 0035396 | 9/1981 | European Pat. Off. |
| 0035397 | 9/1981 | European Pat. Off. |
| 0035398 | 9/1981 | European Pat. Off. |

OTHER PUBLICATIONS

J. C. Giddings, "A New Separation Concept . . . ", Separation Science, 1(1), 123.-125 (1966).
Kirkland et al., "Time-Delayed Exponential . . . ", Analytical Chemistry, 1981, 53, 1730–1736.
Berg and Purcell, "A Method for Separating . . . ", Physics, vol. 58, No. 5, 11/15/67, pp. 18, 21–1828.

Primary Examiner—John Adee
Attorney, Agent, or Firm—Cushman, Darby & Cushman

[57] ABSTRACT

Sedimentation field flow fractionation apparatus having a rotor-mounted fractionation column, has detectors positioned to observe the fluids form the column while still in the rotor. Designs include parallel reference and fractionation columns having their outflows compared in a rotor-mounted fluid flow density balance. Optionally weired channel columns provide a free fluid surface for more efficient resolution. Horizontal rotational axes are preferred. Rotor-mounted fluid flow density balances are also provided which are suitable for detecting liquid density changes in the other applications, such as liquid chromatography.

14 Claims, 4 Drawing Figures

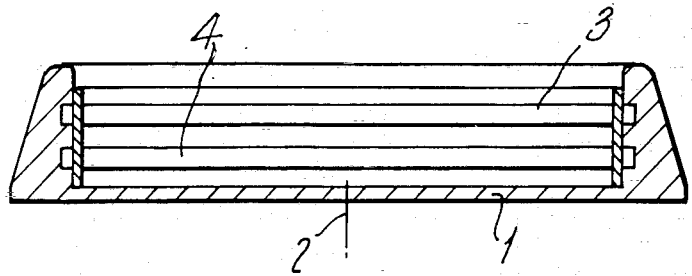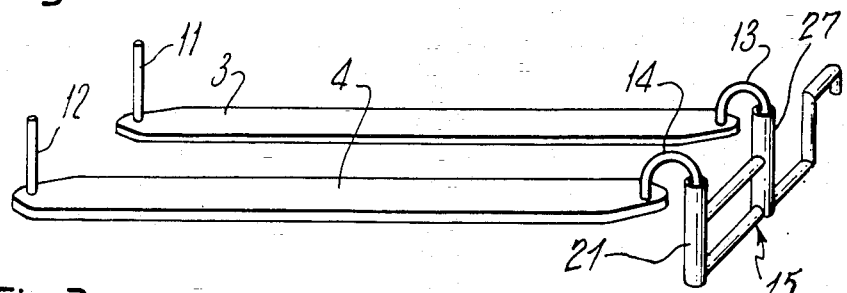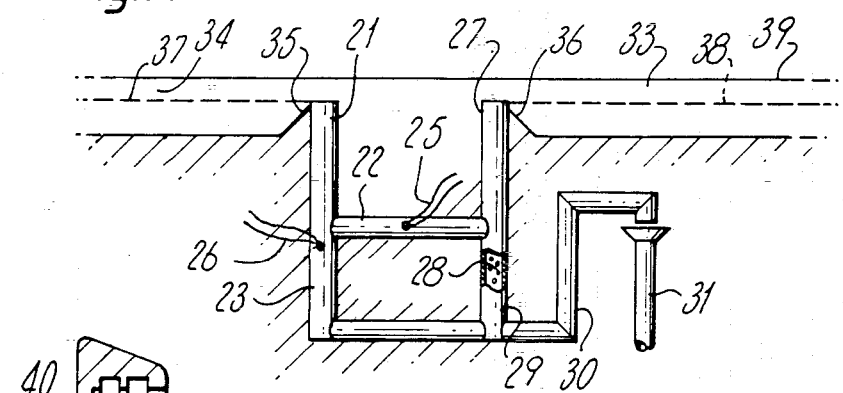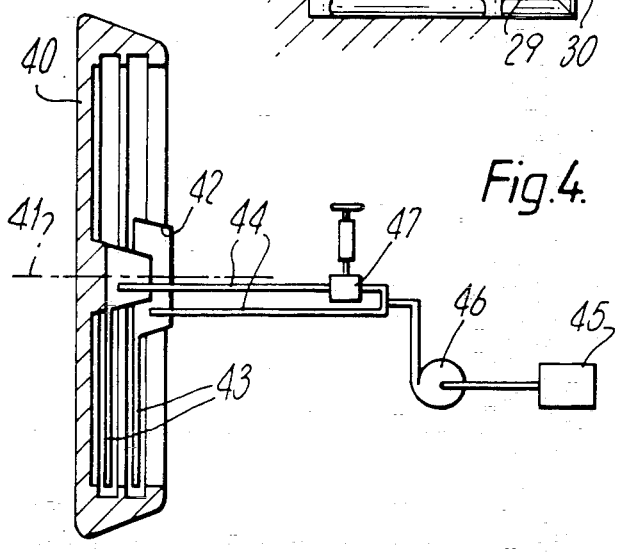

SEDIMENTATION FIELD FLOW FRACTIONATION

The invention relates to apparatus for conducting field flow fractionation by sedimentation, and to a detector suitable for use in the apparatus.

Field flow fractionation (FFF) is a method for separating different species of small particles or macromolecules from a mixture, or identifying individual samples, using flow-elution techniques, and is believed to have been first proposed in 1966 by J C Giddings (Separation Science, 1, 123 (1966)). The mixed species are introduced into a narrow column through which fluid eluent passes with unidirectional laminar flow (i.e. having transverse velocity gradients) and a transverse field is applied to drive the mixed species into the slower moving eluent layers adjacent the column walls. This is balanced by diffusion into the faster eluent layers to a degree which is characteristic of the particular species involved. This gives rise to zones of each species migrating along the column at different velocities depending on the degree of their penetration into the faster solute layers.

In sedimentation field flow fractionation (SFFF) the field is gravitational and is provided by using a centrifuge, a suitable apparatus comprising a rotor rotatable about an axis, a fractionating column mounted in or integral with the rotor, spaced inlet and outlet means mounted in or integral with the rotor for enabling fluid eluent to be fed to the column and to flow therethrough, means for feeding a sample material or mixture of component materials into the eluent and means for detecting the sample or part thereof in the fluid after it has passed through the column. In a typical modern apparatus the column comprises a thin rectangular-sectioned tube positioned with its longitudinal dimension curved at least part way around the rotational axis of the centrifuge so that fluid flowing from one end of the column to the other flow circumferentially around the axis. Fluid is fed to the inlet means from a stationary reservoir, and fluid from the outlet means is piped to a stationary detector. However, this requires seals at the rotary/stationary interface in both the fluid feed and outflow lines, which are capable of withstanding high operating speeds for useful periods and which are of a low volume so as to avoid spreading of the sample zones by longitudinal mixing when transferring the outlet stream from the rotor to the stationary detector. The provision of satisfactory seals presents considerable problems, and much of the published development work on SFFF apparatus since 1966 has been directed to improving the seals. Even though modern designs may be capable of operating at speeds as high as 20,000 rpm to produce fields of 50,000 gravities (e.g. as described in Analytical Chemistry, 53, October 1981, 1730-1736), the difficulties in designing high speed seals and in using them in practical situations, especially under commercial preparative constraints, still limits wider application of these techniques.

According to a first aspect of the present invention, there is provided a sedimentation field flow fractionation apparatus comprising a rotor rotatable about an axis, a fractionation column mounted in or integral with the rotor, spaced inlet and outlet means mounted in or integral with the rotor for enabling fluid eluent to be fed to the column and to flow therethrough, means for feeding a sample into the eluent so that the sample and eluent are caused to flow together through the column while the rotor rotates and subjects the flowing eluent/sample mixture to a transverse gravitational field, and means for detecting the sample or component thereof in the fluid after it has passed through the column, characterised in that the detection means comprises means for responding to the presence of the sample or component thereof within the fluid while it flows through the outlet means in the rotor.

After the sample has been detected by the detection means, it can be discharged from the outlet means in any convenient manner, e.g. by releasing it from an outer edge of the rotor. Hence there is no longer any need to transfer the fluid (without longitudinal mixing) from the rapidly rotating rotor to a stationary part of the apparatus, and the previous requirement for sophisticated but vulnerable high speed seals in the fluid outflow line is avoided. Moreover the seals in the fluid feed lines which were previously necessary to retain sufficient fluid pressure to pump the outgoing fluid against the generated centrifugal forces, can also be dispensed with when discharging the fluid from the outer edge of the rotor.

In order to detect a sample within the fluid while it flows through the outer mass in the rotor, in accordance with the present invention, it is generally necessary for at least part of the detection means to be mounted in or integral with the rotor, but we prefer to keep this to a minimum. Thus a preferred apparatus is one in which the detection means comprises a detector mounted in or integral with the rotor, at least one ancillary device located in a stationary part of the apparatus, and means for conveying information from the detector on the rotor to the stationary ancillary device.

For example, the detector may typically be a fibre optic transmitter/receiver pair mounted on opposite sides of the channel to detect samples or portions thereof flowing between them. The ancillary devices located in a stationary part of the apparatus may then include, for example, light sources, light sensitive receptors, displays, recorders and power sources for the detector, as appropriate. With very high speed rotors in particular, we prefer that the means for conveying information from the detector to stationary ancillary devices comprises means for transmitting and receiving signals across the interface between the rotor and the stationary ancillary device, the transmitting and receiving means being spaced apart with an air gap there between. Thus optical signals can be transmitted across an air gap from one optical fibre to another, for example, preferably using lenses to broaden the light path. Alternating electrical signals and indeed electrical power for the detector can also be induced across an air gap to avoid direct mechanical contact between the rapidly spinning rotor and the stationary parts.

The column is preferably positioned with its longitudinal direction curved around the rotational axis substantially without axial deviation except as may be required to achieve helical configuration where the column completes more than one revolution around that axis.

A preferred apparatus is one having, in addition to the fractionating column, a reference column with inlet and outlet means mounted on or integral with the rotor, and a detector comprising means for balancing a physical property, or signal transduced therefrom, of the fluid which flows through the fractionating column outlet means with that of the fluid which flows through the reference column outlet means, and means for detecting any imbalance. The reference column can have substantially zero length as no fractionation takes place therein. However, we prefer to use a reference column having a configuration corresponding to that of the fractionating column in order to subject fluid flowing therethrough to substantially the same conditions.

The columns can be tubular and of a thin rectangular cross-section, e.g. in conventional manner. However, the present invention enables one effectively to use a fractionating column comprising a channel having a base and sides extending inwards from the base towards the axis of the rotor, thereby to enable liquids to flow along the column as a layer on the base of the channel with a free surface towards the axis. The liquid layer can therefore be of variable depth, dependent inter alia on the rate of rotation, with the centrifugally induced forces being balanced by the surface tension at the end of the column. Where a thicker layer of liquid is desired, this can be provided by an outlet means comprising an inwardly extending weir over which fluid within the channel must flow to escape therefrom, the weir extending inwards from the base by an amount less than that of the sides, thereby to enable the channel to contain a layer of liquid whose depth is controlled by the degree of inward extension of the weir, while rotor liquid is being rotated.

When using a column comprising an open channel, we prefer to mount the rotor with its axis of rotation horizontal. This has an advantage in that normal gravity then acts evenly across the width of the channel and so does not affect the constancy of the fluid depth across the channel. Where a vertical axis is used, i.e. as has previously been used in known SFFF apparatus, normal gravity acts continuously across the channel and so will produce a greater fluid depth at the lower edge. Even though the centrifugal forces may be very considerably greater, even a shallow surface angle in a very thin stream, e.g. 125 $\mu$m, in a usefully wide channel, e.g. 2 cm, can significantly affect the depth across channel width. The effect of such variation is a loss in resolving power of the instrument.

A further preferment is to provide the open channel with a cover, thereby to protect any thin layer of liquid within the channel from being disturbed by the surrounding air during rotation of the rotor. The cover being held clear of the surface of the liquid as it flows along the column.

A preferred detector which can be conveniently mounted in the rotor or integrally formed therein comprises a flowing fluid density balance wherein the fluid flow from the reference column is split and balanced against the flow from the fractionation column such that a change in density of the latter varies the relative flow rates of the split portions of the reference fluid.

Various designs of flowing fluid density balances have previously been described for balancing gas densities (e.g. as described in U.S. Pat. No. 3,050,984), but under normal gravity conditions, such known detectors are not sufficiently sensitive when used with liquids, due to the much higher viscosities of the latter, for them to have found much application outside their use with gases. However, we have now found that by mounting a fluid flow density balance in a centrifuge so as to replace the normal gravitational forces due to the Earth's gravitational field, with those generated by rotation of the centrifuge, an apparatus can be provided which is sensitive even to very small changes in liquid densities, whether these changes be due to the inclusion of a second miscible liquid, dissolved solute or fine suspended solids, for example.

The very high gravitational fields employed in SFFF make it a particularly suitable application for centrifuge-mounted fluid density balances, but this is not the only possible application. Other analytical and preparative processes involving liquids whose densities vary, e.g. through the presence of a further substance, may also employ such a detector with advantage. Such processes include liquid chromatography, for example. Indeed, we find that a fluid flow density balance mounted in its own centrifuge can even be used to advantage with conventional SFFF apparatus, in which the fluid from the fractionating column is fed via seals across the rotating/stationary interface to one arm of the separately rotating density balance, while reference liquid is fed to a balancing arm.

Accordingly we now provide as a further aspect of the present invention, an apparatus for detecting changes in the density of a first liquid, which comprises a centrifuge having a rotor, and a flowing fluid density balance for balancing the density of the first liquid with that of a reference second liquid, the flowing fluid density being mounted on or integral with the rotor such that the densities to be balanced are the effective densities in the gravitational field generated by rotation of the rotor, the apparatus also having means for feeding the first and second liquids to the density balance while the rotor is rotating. Thus to be operable in the present apparatus, a density balance designed to be used vertically (i.e. with an upper and a lower portion) in the Earth's gravitational field, e.g. for balancing gas densities, needs to be oriented radially with respect to the rotor's axis of rotation, with its lower portion more remote from the axis than the upper portion.

The means for feeding the first and second liquids to the density balance in this further aspect of the invention, may be substantially as described herein for the SFFF apparatus, but preferably without a column for any significant length as the latter may reduce resolution through introduction of dead space and delay of dense materials. An advantage of the density balance as a means for detecting density changes in liquids is the very small internal volume which can be achieved. This can provide a resolution smaller than a single free drop of liquid, which would therefore restrict the resolution that could be achieved by the apparatus in practice, and we have devised a means for feeding the first liquid to the density balance without such limitations.

Our preferred apparatus is therefore one in which the means for feeding the first liquid to the density balance comprises a stationary supply conduit terminating in an end portion for expressing liquid therethrough, and a projection positioned on the rotor so as to intercept any liquid being expressed from the end portion of the supply conduit and remove a sample of the expressed liquid during each revolution of the rotor, the density balance being positioned in the rotor with respect to the projection so as to receive each of the samples removed. The reference second liquid is also preferably fed to the density balance in like manner, although the size of increment is less critical for the second liquid than for the first.

The invention is illustrated by reference to specific embodiments thereof shown in the accompanying drawings, in which FIG. 1 is a schematic section through an SFFF apparatus having both fractionation and reference columns, FIG. 2 shows the two columns laid out flat and overflowing into a rotor-mounted detector, FIG. 3 is a section through the detector, fed from alternative column designs, FIG. 4 is a sketch showing inlet means for the columns shown in FIG. 3;

FIG. 5 is an oblique view of the apparatus of FIGS. 3 and 4 and illustrating the curvature of the columns around the innerface of the rotor.

The apparatus shown in FIG. 1 comprises a centrifuge rotor 1, rotatable about a vertical axis 2, and carrying two parallel columns 3, 4. These have been formed by machining two channels in the wall of the rotor and closing these with plates to form two tubes extending almost round the rotor until the two ends (not shown in FIG. 1) are adjacent. In use the rotor is rotated at high speed to create a radial gravitational field.

The two columns 3, 4 are also depicted in FIG. 2 where they have been shown straightened out for explanation purposes, and orientated so that the direction of the centrifugal gravitational field is vertically downwards. The columns in FIG. 2 are shown with inlet tubes 11, 12 sealed into the tubular columns at one end. At the other end of each is an overflow pipe 13, 14, so that fluid eluent poured into either of the inlet tubes will flow through the column and out through the overflow pipe, so long as fluid feed is continued to maintain sufficient head of liquid in the inlet tube. The outflows from the overflow pipes are the inlets 21, 27 for two arms of a flowing fluid density balance 15.

The same balance 15 is also shown in FIG. 3, in elevation for greater clarity. It comprises a reference fluid inlet 21, which splits to provide an upper reference arm 22 and a lower reference arm 23, both of which carry thermister flow sensors 25, 26, (whose temperatures are reduced by increased flow rate). These are balanced in a bridge network (not shown). The other inlet 27 is positioned to receive fluid from the fractionating column, that fluid comprising eluent, and at times a more dense zone 28 containing the sample or fraction to be detected. That other inlet tube enters a balance tube 29 which interconnects the split reference arms 22, 23 at its upper and lower ends respectively. An outlet 30 is also connected to the lower end of the balance tube.

Initially, fluid from the fractionating column is pure eluent, and the two thermister outputs are balanced. When the denser zone 28 reaches the balance tube 29, the total density of the right hand column of fluid becomes greater than that of the left hand column, thereby inducing a clockwise flow component on the fluid in the tubes 22, 23 and 29 forming the rectangular configuration in the lower part of the balance. This clockwise component in practice is generally small compared with the flow rate of reference fluid, and the practical effect is that a slightly higher proportion of the reference fluid flows through the upper reference arm 22 and a correspondingly lower proportion flows through the lower reference arm 23, thereby causing an imbalance in the bridge network.

The output means continues with the common outlet tube 30, which can be positioned to discharge through the base of the rotor. However, in the apparatus shown it was preferred to discharge the fluids from the outer edge of the rotor, and a separate discharge tube 31 has been added with a break between the outlet and discharge tubes to avoid syphoning the fluids from the balance.

In FIG. 3, the two columns 33, 34 have been drawn with their longitudinal axes in the plane of the paper to show their outflow details, whereas in practice they have a parallel configuration orthogonal to the plane of the balance, i.e. as shown in FIG. 2. However, they differ from the columns of FIG. 2 in having a weir 35, 36 at their outlet ends instead of an overflow pipe. Hence instead of filling the tubular column with fluids, as in the apparatus of FIG. 2, the fluid level 37, 38 in each column is determined by the height of the weir, i.e. by how far the weir extends towards the axis of rotation from the base of the channel forming the column. (As described above the presence of a weir is not always necessary, as surface tension alone may provide sufficient depth in some liquids).

An alternative to the use of flow rate sensing thermisters in the two reference legs and their attendant balancing bridge circuit, is to measure the amount of flow though the upper reference arm as a proportion of the amount of total flow through the balance tube 29. This can be measured by doping the reference fluid with some form of optical marker, e.g. an absorbing or fluorescing dye or light scattering material, and detecting the amount of marker flowing through the balance tube, e.g. using an optical emitter/detector pair. When there is no sample in the balance tube, the proportion of reference fluid flowing through the upper and lower arms is constant, so that the proportion of colour or other marker in the balance tube remains constant. Indeed it can be adjusted to be zero when no sample is present, but there is then danger of incurring an end error when initial traces of sample arrive, so we prefer to have a small flow of marker when no sample is flowing. On arrival of sample in the balance tube, a clockwise flow component is induced as before, and more marker flows into the balance tube 29. Thus the proportion of marker in the fluid flowing through the balance tube is a function of the amount of sample in that balance tube.

As the sample also flows through the balance tube, there is the possibility that it also might affect the detection of the marker by absorbing or scattering non-linearly. This could then be overcome by using two light beams of different but close wavelengths whose relative absorptions by the marker are different from those for the sample.

In FIGS. 4 and 5, the channels of the columns 33, 34 are machined in a rotor 40 which is mounted to rotate about a horizontal axis 41. Inlet means comprising conical funnels 42 and thin inlet tubes 43 extending tangentially from the bases of the funnels to the channels, are mounted in the rotor to rotate with it. Stationary feed pipes 44 are connected to an eluent reservoir 45 via a pump 46, and a sample injector 47 is provided in one feed tube. Fluids pumped through the stationary feed pipes into their respective rotating funnels, are caused to flow outwards to the channels through the thin inlet pipes by centrifugal forces generated by rotation of the rotor about the axis 41. The stationary equipment 44-47 for delivering eluent and sample to the cones 42 has been omitted from FIG. 5 in order to avoid obscuring the inlets and outlets of the channels 33, 34. The ends of the channels are tapered similar to those shown in FIG. 2. The thin inlet tubes 44 extend to deliver their eluent to one tapered end of each channel. At the other end, the channel becomes abruptly shallower so as to form the weir 35 shown in section in FIG. 3, and of the inlet tubes 21, 27 of the density balance (which extends radially outwards from the end of the weir), only the open ends 21', 27' are seen in the view shown in FIG. 5, the remainder of the balance being hidden by the body of the rotor 40.

Other methods of feeding the fluids to the channels are also possible. For example, with the horizontal axis of rotation in FIG. 4, if the funnels 42 are removed, the feed pipes 44 can be lined up with the channels so that fluid can flow downwards as a free stream instead of flowing through tubes 43. In order that this reaches only the inlet end of the channel forming the column 33, 34 in each case, that end of the channel is extended radially inwards so as to catch a portion of the falling stream of fluid each time it reaches the stream through rotation of the rotor. The length of the inward extension is determined by the rate of rotation such that it is at least as long as the distance fallen by the fluid during each revolution of the rotor. Hence all the fluid is caught as a large number of very small portions (at least in a high reving centrifuge).

We claim:

1. Sedimentation field flow fractionation apparatus comprising a rotor rotatable about an axis, a fractionation column mounted on or integral with the rotor, spaced inlet and outlet means mounted in or integral with the rotor for enabling fluid eluent to be fed to the column and to flow therethrough, means for feeding a sample into the eluent so that the sample and eluent are caused to flow together through the column while the rotor rotates and subjects the flowing eluent/sample mixture to a transverse gravitational field, and means for detecting the sample or component therefore in the fluid leaving the column, characterised in that the detecting means comprises means for responding to the presence of the sample or component therefore within the fluid while the fluid flows through the outlet means in the rotor.

2. Apparatus as claimed in claim 1 wherein the detecting means comprises a detector which is mounted on or is integral with the rotor, at least one ancillary device located in a stationary part of the apparatus, and means for conveying information from the detector on the rotor to the stationary ancillary device.

3. Apparatus as claimed in claim 2 in which the means for conveying information from the detector to stationary ancillary devices comprises means for transmitting and receiving signals across the interface between the rotor and the stationary ancillary device, the transmitting and receiving means being spaced apart with an air gap therebetween.

4. Apparatus as claimed in any one of the preceding claims, in which there is also provided a reference column with inlet and outlet means mounted on or integral with the rotor, and a detector means for balancing a physical property, or signal transduced therefrom, of the fluid which flows through the fractionating column outlet means with that of the fluid which flows through the reference column outlet means, and means for detecting any imbalance.

5. Apparatus as claimed in claim 1 in which the fractionation column comprises a channel having a base and sides extending inwards from the base towards the axis of the rotor, thereby to enable liquids to flow along the column as a layer on the base of the channel with a free surface towards the axis.

6. Apparatus as claimed in claim 5, in which the fractionating column has an outlet means comprising an inwardly extending weir over which fluid within the channel must flow to escape therefrom, the weir extending inwards from the base by an amount less than that of the sides, thereby to enable the channel to contain a layer of liquid whose depth is controlled by the degree of inward extension of the weir, while the rotor is being rotated.

7. Apparatus as claimed in claim 5 or claim 6 in which the rotor is mounted with its axis of rotation horizontal.

8. Apparatus as claimed in claims 5 or 6 in which the open channel is provided with a cover thereby to protect any layer of liquid within the channel from being disturbed by the surrounding air during rotation of the rotor, the cover being held clear of the surface of the liquid as it flows along the column.

9. Apparatus as claimed in claim 4 in which the detector comprises a flowing fluid density balance wherein the fluid flow from the reference column is split and balanced against a flow from the fractionation column such that a change in density of the latter varies the relative flow rates of the split portions of the reference fluid.

10. Apparatus for detecting changes in the density of a first liquid, which comprises a centrifuge having a rotor, and a flowing fluid density balance for balancing the density of the first liquid with that of a reference second liquid, the flowing fluid density balance being mounted on or integral with the rotor such that the densities to be balanced are the effective densities in the gravitational field generated by rotation of the rotor, the apparatus also having means for feeding the first and second liquids to the density balance while the rotor is rotating.

11. Apparatus as claimed in claim 10 in which the means for feeding the first liquid to the density balance comprises a stationary supply conduit terminating in an end portion for expressing liquid therethrough, and a projection positioned on the rotor so as to intercept any liquid being expressed from the end portion of the supply conduit and remove a sample of the expressed liquid during each revolution of the rotor, the density balance being positioned in the rotor with respect to them projection so as to receive each of the samples removed.

12. Apparatus as recited in claim 2 in which the fractionation column comprises a channel having a base and sides extending inwards from the base towards the axis of the rotor, thereby to enable liquids to flow along the column as a layer on the base of the channel with a free surface towards the axis.

13. Apparatus as recited in claim 3 in which the fractionation column comprises a channel having a base and sides extending inwarrds from the base towards the axis of the rotor, thereby to enable liquids to flow along the column as a layer on the base of the channel with a free surface towards the axis.

14. Apparatus as recited in claim 6 in which the rotor is mounted with its axis of rotation horizontal, and in which the open channel is provided with a cover to protect any layer of liquid within the channel from being disturbed by the surrounding air during rotation of the rotor, the cover being held clear of the surface of the liquid as it flows along the column.

* * * * *